United States Patent [19]

Tarr et al.

[11] Patent Number: 5,243,983
[45] Date of Patent: Sep. 14, 1993

[54] NON-INVASIVE BLOOD GLUCOSE MEASUREMENT SYSTEM AND METHOD USING STIMULATED RAMAN SPECTROSCOPY

[75] Inventors: Randall V. Tarr, Atlanta; Paul G. Steffes, Norcross, both of Ga.

[73] Assignee: Georgia Tech Research Corporation, Atlanta, Ga.

[21] Appl. No.: 627,631

[22] Filed: Dec. 14, 1990

[51] Int. Cl.$^5$ .................... A61B 5/00; A61B 3/10; G01N 33/483; G01J 3/44
[52] U.S. Cl. .................... 128/633; 356/301; 356/39; 351/221
[58] Field of Search ........ 128/633, 664, 665; 356/41, 301, 39; 351/221

[56] References Cited

U.S. PATENT DOCUMENTS

| | | | |
|---|---|---|---|
| 3,802,777 | 4/1974 | Regnier et al. | 356/301 |
| 4,620,284 | 10/1986 | Schnell et al. | 364/498 |
| 4,648,714 | 3/1987 | Benner et al. | 356/301 |
| 4,676,639 | 6/1987 | Van Wagenen | 356/246 |
| 4,758,081 | 7/1988 | Barnes | 606/4 |
| 4,832,483 | 5/1989 | Verma | 356/39 |
| 5,025,785 | 6/1991 | Weiss | 128/633 |

Primary Examiner—Lee S. Cohen
Assistant Examiner—Kevin Pontius
Attorney, Agent, or Firm—Deveau, Colton & Marquis

[57] ABSTRACT

Stimulated Raman spectroscopy is used to non-invasively measure the concentration of an Raman active molecule, preferably D-glucose in the ocular aqueous humor of living being. The apparatus and method make use of two monochromatic laser beams, a pump laser beam and a probe laser beam. The output power of the pump laser beam is amplitude modulated, combined with the probe laser beam and directed into the ocular aqueous humor. The introduction of the laser beams into the ocular aqueous humor induces scattered Raman radiation, which causes a portion of the energy at the pump frequency to shift over to the probe frequency. The pump and probe laser beams are then detected as they exit the ocular aqueous humor. The probe laser beam is filtered, converted into an electrical signal and amplified. It is then compared to the modulation signal to generate an electrical signal representative of the concentration of D-glucose in the ocular aqueous humor.

32 Claims, 6 Drawing Sheets

NON-INVASIVE BLOOD GLUCOSE MEASUREMENT SYSTEM AND METHOD USING STIMULATED RAMAN SPECTROSCOPY

BACKGROUND OF THE INVENTION

A. Field of the Invention

The present invention relates to a non-invasive method and apparatus for measuring the concentration of D-glucose in the ocular aqueous humor. More particularly, the present invention is a non-invasive technique for the in vivo measurement of the glucose concentration in the ocular aqueous humor employing the stimulated Raman effect.

B. Background of the Invention

Diabetes Mellitus is a major health problem in the world today because of the physical complications which arise from living many years with above-normal blood glucose levels. Currently, over 11 million people suffer from diabetes in the United States alone. The two most common forms of diabetes are Type I, juvenile-onset, and Type II, adult-onset. Type I diabetes destroys the vast majority of the insulin-producing beta cells in the pancreas, forcing its sufferers to take multiple daily insulin injections. Type II diabetes is usually less severe than Type I as some endogenous insulin production still occurs and, as a result, type II diabetes can often be controlled by diet alone.

The body requires insulin for many metabolic processes; it is particularly important to the metabolism of glucose. It is believed that many of the physical complications associated with diabetes could be avoided if normal blood glucose levels were maintained throughout each day. A diabetic's blood glucose level can fluctuate widely around each meal. Maintaining normal blood glucose levels and reducing these fluctuations requires using some form of feedback to regulate the multiple daily insulin shots of Type I diabetics or the diet of type II diabetics.

Currently, the blood glucose level can be determined by a chemical reaction performed on a blood sample. Although the state of the art glucose measurement devices are very accurate, the need for a blood sample for each measurement limits their utility. The most dedicated diabetic patient may take only 4 or 5 measurements per day, and many diabetics perform even fewer. Because a diabetic's blood glucose level can fluctuate by a factor of two or more in a period of an hour, this method cannot provide the feedback necessary to maintain a normal blood glucose level throughout the day.

A non-invasive blood glucose measurement technique would allow a large number of daily measurements to be taken without the problems associated with taking blood samples. Various schemes have been attempted to non-invasively measure blood glucose level. Many promising techniques attempt to measure the glucose level in the ocular aqueous humor because it has been shown that the ocular glucose level directly correlates to the blood glucose level and because the ocular aqueous humor provides a much simpler spectroscopic environment than the blood.

D-glucose occurs normally and in abundance in both the blood and the ocular aqueous humor. There are two anomers of D-glucose found in nature: $\alpha$-D-glucose and $\beta$-D-glucose, which differ only in the orientation of the groups attached to the C-1 carbon. Physically, these two anomers of D-glucose can be distinguished by their optical activity; i.e. based upon their ability to rotate the plane of polarization when illuminated with plane polarized light. In general, the specific rotation, $[\alpha]$, is defined as $$[\alpha] = \frac{\alpha}{\iota d} \tag{1}$$

where $\alpha$ is the total optical rotation of the plane of polarization measured in degrees, $\iota$ is the length of the sample in decimeters, and d is the density in g/cm$^3$. The specific rotations of $\alpha$-D-glucose and $\beta$-D-glucose are 112 and 19 degrees, respectively. In solution, one anomer is converted into the other as necessary to achieve an equilibrium solution which has a specific rotation of 52.7 degrees.

Since the specific rotation of D-glucose in solution is known, from Equation (1) one can infer the concentration of D-glucose in a given sample by measuring the total optical rotation. The accuracy and linearity observed at very low D-glucose concentrations led March et al. to attempt non-invasive measurements in the eyes of rabbits. See Rabinovitch, March and Adams, *Non-invasive Glucose Monitoring of the Aqueous Humor of the Eye: Part I. Measurements of Very Small Optical Rotations*, 5 Diabetes Care 1254 (May–June 1982); March, Rabinovitch and Adams, *Non-invasive Glucose Monitoring of the Aqueous Humor of the Eye: Part II, Animal Studies and the Scleral Lens*, 5 Diabetes Care 259 (May–June 1982). Unfortunately, March and his colleagues experienced great difficulty in measuring the concentration of D-glucose in the ocular aqueous humor. Many compounds in the ocular aqueous humor other than D-glucose are optically active and contribute to the rotation of the plane of polarization. In addition, the cornea has birefringence, which causes a further rotation of the plane of polarization of the incident light. See generally, Gough, *The Composition of and Optical Rotary Dispersion of Bovine Aqueous Humour*, 5 Diabetes Care 266 (May–June 1982).

Both spontaneous and stimulated Raman spectroscopy are potentially useful to measure the concentration of an Raman active molecule in a medium. With spontaneous Raman spectroscopy a monochromatic laser beam is directed into a Raman-active medium. Some of the incident beam is transmitted, some of it is absorbed, and some of it is scattered. A small fraction of the radiation scattered is shifted in frequency from the incident beam. The amount of this relative frequency shift is related to the vibrational states of the Raman active molecules in the medium. The problem with spontaneous Raman scattering is that the Raman power is scattered in all directions. This makes the detection of the scattered radiation difficult for in vivo measurements.

Stimulated Raman spectroscopy (SRS) directs two monochromatic laser beams, a pump laser beam and a probe laser beam, into a Raman active medium. If the power of the pump laser is modulated, then the spontaneous Raman scattered power will also be modulated, which will induce a signal on the probe laser beam. Thus, rather than measuring the spontaneous Raman scattered power directly, a measurement of an intensity fluctuation of the probe laser beam can be made.

Stimulated Raman spectroscopy has been successfully used to measure very low concentrations of certain selected organic liquids diluted by water and other solvents. Owyoung and Jones performed a series of experiments with benzene using stimulated Raman scattering techniques. See, Owyoung, *Sensitivity Limitations for CW Stimulated Raman Spectroscopy*, 22 Optics Communications 323 (September 1977); Owyoung and Jones, *Stimulated Raman Spectroscopy Using Low-Power CW Lasers*, 1 Optics Letters 152 (November 1977). Their experimental set-up consisted of two lasers, a tunable pump laser and a fixed frequency probe laser. The pump laser Power was modulated while the probe laser power was held constant. The two laser beams were combined and focused through a benzene cell. In the cell the stimulated Raman effect caused a very small fraction of the Power at the pump wavelength to be shifted to the probe wavelength. Thus, at the output of the benzene cell the probe laser beam carried a small modulation signal whose amplitude was directly proportional to the concentration of the benzene in the cell. The probe wavelength was separated from the pump and converted to an electrical signal by a photodiode. Both the probe signal and the input pump modulation signal were fed into a synchronous detector which greatly improved the signal-to-noise ratio. The pump laser is then repeatedly tuned to new wavelengths to scan a range of wavelengths, thus, obtaining a Raman spectra for the Raman-active liquid or gas. This is the same type of spectrum obtainable by using a commercially available Raman spectrometer.

Until the present invention, no one has developed a technique which would allow for non-invasive in vivo measurement of the glucose concentration in the ocular aqueous humor. March attempted a non-invasive technique employing an energy wave transmitter, such as an infrared source located on one side of the cornea and an associated detector on the opposite side of the cornea. See U.S. Pat. No. 3,958,650. The wave source is aimed to cause the radiation to pass through the cornea and the aqueous humor to the detector. A transmitter is mounted adjacent to the detector and coupled thereto for transmitting a signal that is a function of the radiation level detected. This technique is seriously flawed. The radiation detected will be a function of the concentration of all substituents in the humor, not just glucose. The later optical rotation technique of March, Rabinovitch and Adams suffers from a similar flaw. Further, no one, until now, has determined whether stimulated Raman spectroscopy may be successfully used to measure concentrations of glucose in the ocular aqueous humor.

SUMMARY OF THE INVENTION

A non-invasive blood glucose measurement technique would allow more frequent measurement of blood glucose concentrations without the problems associated with taking blood samples. The present invention achieves this goal by providing an apparatus and a method for non-invasively measuring the in vivo concentration of an Raman active molecule in the ocular aqueous humor by using stimulated Raman spectroscopy. The apparatus of the present invention includes a means for emitting a probe laser beam and a means for emitting a pump laser beam. Both means emit monochromatic laser light and are separated in wavelength by a wavelength chosen to be within a characteristic Raman shift spectrum for the Raman active molecule. By setting the separation in wavelength between the pump and probe lasers, one may select which one of a number of Raman active molecules will be measured. In the preferred embodiment the selected Raman active molecule is D-glucose and the separation between the probe wavelength and pump wavelength is chosen to be 518 cm$^{-1}$ in accordance with the characteristic Raman shift spectrum for D-glucose.

The apparatus also includes a modulating means for modulating the output Power of the pump laser beam. A power source is provided for the probe laser for maintaining its power output substantially constant. The modulated pump laser beam is then combined with the probe laser beam by a means for directing the combined laser beams into the ocular aqueous humor.

The introduction of light into the ocular aqueous humor stimulates Raman radiation which shifts energy from the pump frequency to the probe frequency, thereby inducing fluctuations in the probe laser beam directly related to the concentration of the selected Raman active molecule in the ocular aqueous humor. After the probe laser beam exits the ocular aqueous humor, means are provided for detecting the probe laser beam and converting it into a Raman electrical signal. The Raman electrical signal is then compared to the modulation signal by a synchronous detector, a dynamic signal analyzer, or a computer based synchronous detection system, to produce a voltage representative of the concentration of the Raman active molecule in the ocular aqueous humor.

The method of the present invention non-invasively measures the in vivo concentration of an Raman active molecule in the ocular aqueous humor using stimulated Raman spectroscopy. Two monochromatic laser beams are provided, a probe laser beam and a pump laser beam. The probe laser beam and the pump laser beam wavelengths are separated from each other by a wavelength within a characteristic Raman spectrum for the Raman active molecule being measured. In the preferred embodiment, the Raman active molecule is D-glucose and the separation in frequency preferably chosen to be 518 cm$^{-1}$. The output power of the probe laser beam should be maintained substantially constant, while the output power of the pump laser beam is modulated by a modulation signal. The probe laser beam and the modulated pump laser beam are combined and directed into the ocular aqueous humor, thereby stimulating Raman scattered radiation. The probe laser beam is detected after it exits the ocular aqueous humor and converted into an electrical signal. The electrical signal is then compared with the modulation signal to produce a voltage representative concentration of the Raman active molecule.

It is, therefore, an object of the present invention to provide a system for measuring an Raman active molecule in the ocular aqueous humor.

It is another object of the present invention to provide a system for measuring very small D-glucose concentrations.

It is Yet another object of the present invention to make non-invasive in vivo measurements of D-glucose concentration.

It is a further object of the present invention to allow multiple daily measurements of D-glucose to be made non-invasively.

It is a still further object of the present invention to provide a non-invasive glucose measurement system which is inexpensive to manufacture, durable in construction, and efficient in operation.

These and other advantages will become apparent in the discussion below.

DETAILED DESCRIPTION

When a monochromatic laser beam is incident on a Raman-active medium some of the incident beam is transmitted, some of it is absorbed, and some of it is scattered. A small fraction of the radiation scattered is shifted in frequency from the incident beam. The amount of this relative frequency shift is related to the vibrational states of the molecules in the medium. The D-glucose molecule has several possible Raman active vibrational states so that the Raman scattered power forms a spectrum which is characteristic of D-glucose alone.

Figure 1:
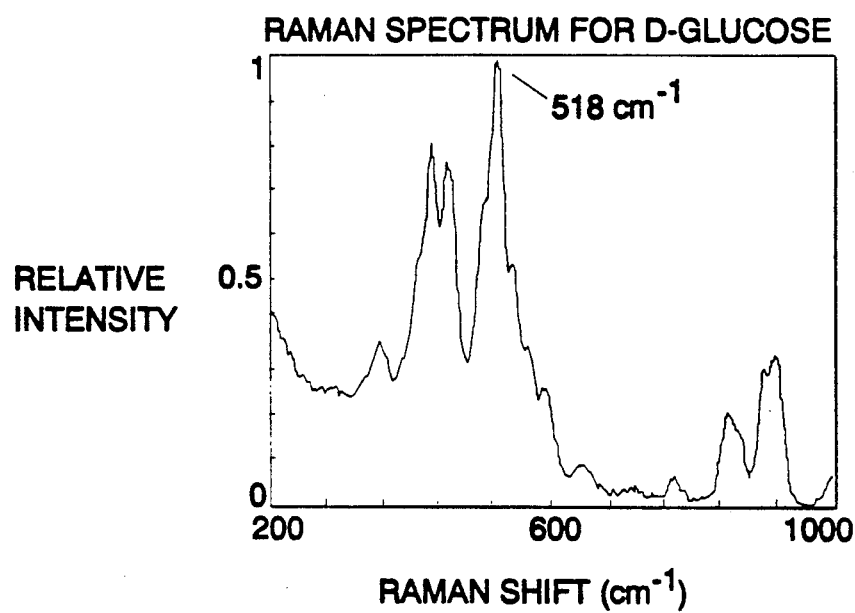
FIG. 1 is a graph of the spontaneous Raman spectrum for D-glucose.

Turning now to the drawings in which like numerals denote corresponding parts the preferred embodiment of the present invention is shown. FIG. 1 illustrates the characteristic spectrum for D-glucose dissolved in water showing the relative intensity of spontaneous Raman power versus the frequency shift. Each of the peaks in the spectrum corresponds to a particular vibration of the D-glucose molecule, the largest peak occurring at a frequency shift of 518 cm$^{-1}$. The absolute intensities of the peaks are directly related to the concentration of the Raman-active molecule, in this case D-glucose.

Figure 2:
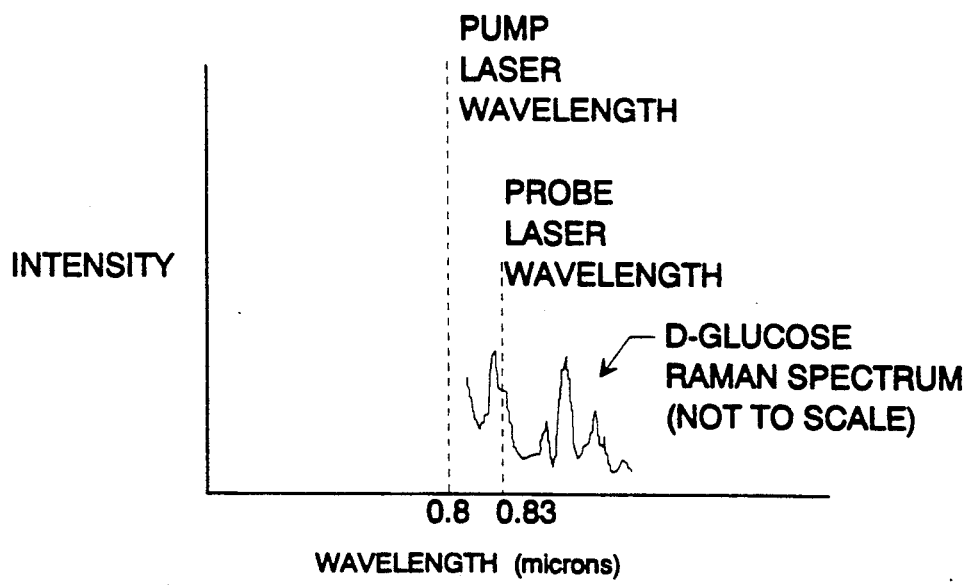
FIG. 2 illustrates the stimulated Raman spectroscopy (SRS) wavelength selection for the preferred embodiment.

Use of a single monochromatic laser beam to generate spontaneous Raman scattering is difficult for in vivo measurements since the Raman power is scattered in all directions. This problem can be solved by having two monochromatic laser beams a pump laser and a probe laser) incident on the chosen sample. Thus, in the preferred embodiment, the probe laser is at the same frequency as the Raman scattered power from a large peak in the D-glucose spectrum, as illustrated in FIG. 2. The pump laser is at a frequency whose difference from the probe frequency is equal to the frequency shift of the large peak selected for the probe laser. In order to use stimulated Raman spectroscopy to measure the concentration of D-glucose in the ocular aqueous humor, the frequency difference between the pump laser beam and the probe laser beam must be chosen to coincide with one of the peaks in the Raman spectrum for D-glucose. If the power output of the pump laser is modulated, then the spontaneous Raman scattered power will also be modulated which will induce a signal on the probe laser beam. Rather than measuring the spontaneous Raman scattered power directly, a measurement of an intensity fluctuation on the probe laser beam is made. This method is called stimulated Raman spectroscopy.

Figure 3:
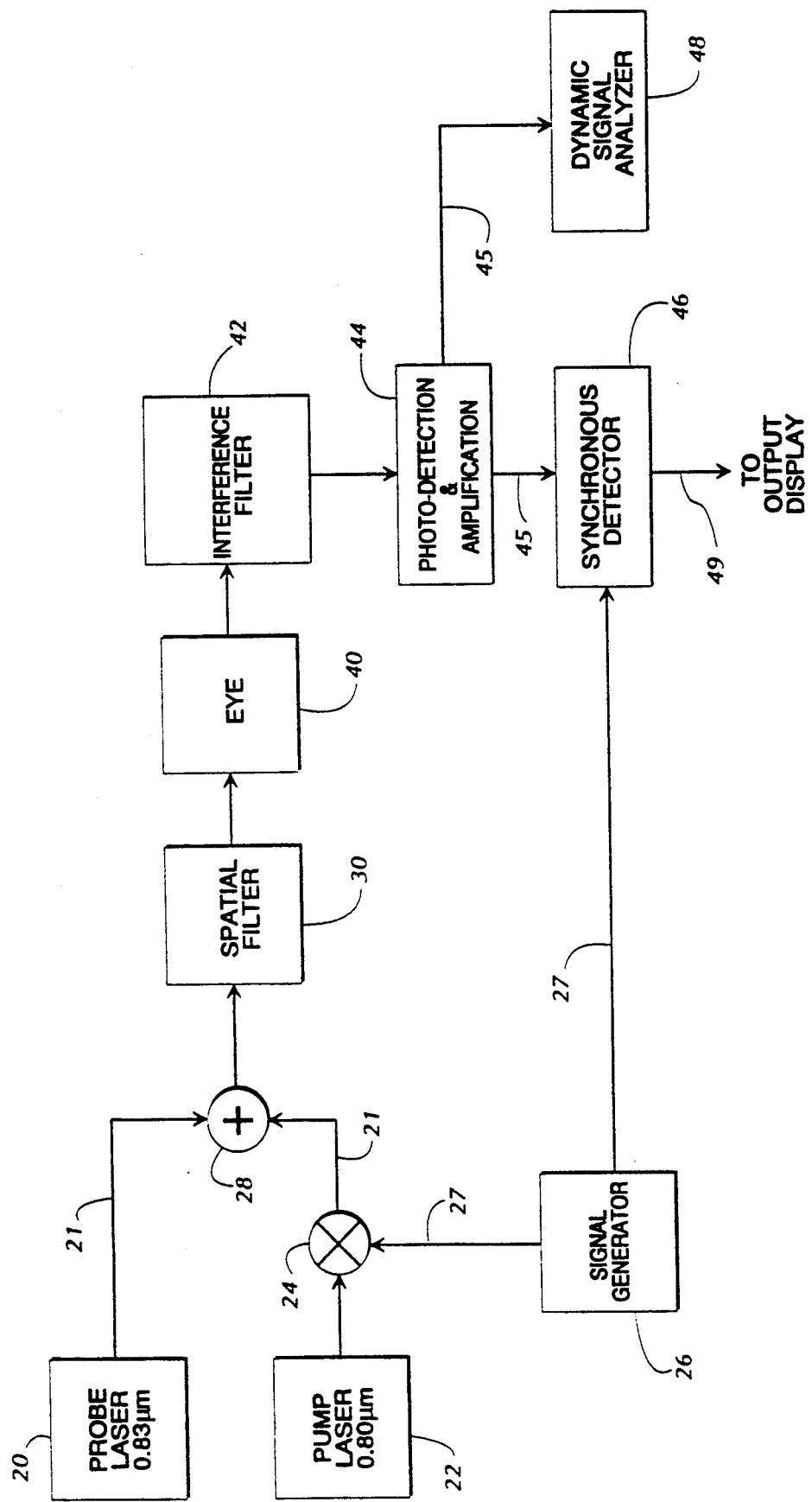
FIG. 3 is a block diagram of one embodiment of the present invention.

As shown in FIG. 3, the present invention involves two lasers, a probe laser 20 and a pump laser 22. Both lasers 20 and 22 emit monochromatic laser beams. The relative wavelength difference between these two laser beams is adjusted to be the same as the wavelength shift of one of the largest spontaneous Raman peaks for D-glucose, 518 cm$^{-1}$. Other peaks unique to the D-glucose spectrum may be chosen, for example, 400 cm$^{-1}$.

The probe laser 20 chosen operates at a wavelength of approximately 0.83 micrometers with an output power of 20 mW. The probe laser power output should remain substantially constant over time in order to minimize errors in measurement. Thus, the sensitivity of the system is directly related to the ability to maintain the probe laser power output constant. The laser diode chosen, an SDL-1401-H2, is slightly tunable with temperature.

The pump laser 22 chosen emits light with a wavelength of approximately 0.8 micrometers and an output power of 100 mW. The power output of the pump laser should ordinarily be greater than that of the probe laser by about 5× depending upon the threshold conditions for the medium. The pump laser wavelength is also slightly tunable with temperature to allow fine adjustment for optimal signal level.

The actual wavelengths chosen for the pump and probe laser beams are not as important as the separation between them. That separation should correspond to a vibrational state of the Raman active molecule being measured. For example, should it be desirable to concentrate on the D-glucose peak at 400 cm$^{-1}$, a different separation would be chosen for the wavelengths output by the probe and pump laws. The particular wavelengths of 0.8 and 0.83 were selected because of the availability of commercial diode lasers of such wavelengths.

Figure 4:
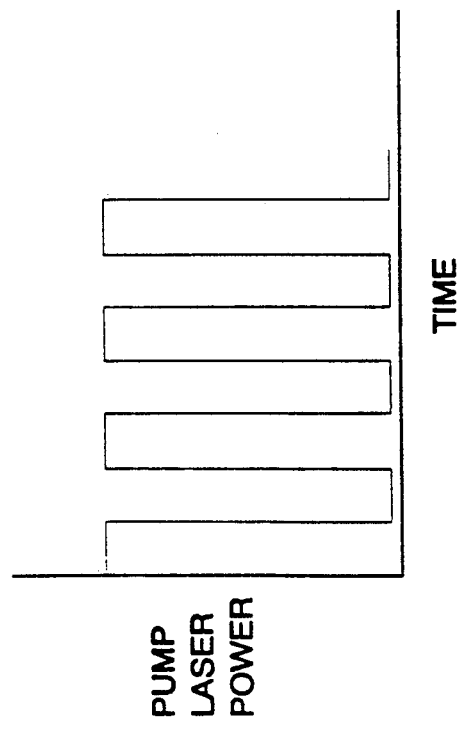
FIG. 4 depicts the preferred amplitude modulation of the pump laser power versus time.

The pump laser beam is amplitude modulated by a biased square wave signal from signal generator 26. The output of signal generator 26 is used to modulate the current to the diode of the pump laser 22 thereby modulating the amplitude of the output of the laser beam. The output of pump laser 22 is a biased square wave, with a maximum amplitude of approximately 100 mW and a minimum of approximately 0 mW. An example of amplitude modulated pump laser power over time is illustrated in FIG. 4.

It is possible to use other types of modulation to measure the concentration of Raman active molecules using stimulated Raman spectroscopy. Amplitude modulation was chosen over other types of modulation, such as pulse width modulation, because amplitude modulation is easier to generate. Further, the type of modulation chosen affects the complexity of the detection scheme that must be used. The choice of modulation technique also affects the power incident upon the eye. Any technique which reduces this power reduces possible damage to the eye and is to be preferred.

The probe laser beam and the amplitude modulated pump laser beam are fed to a fiber optic coupler 28 via fiber optic pigtails 21. Only 50% of the power in the probe and pump laser beams is coupled into the fiber optic pigtails 21 due to their coupling efficiency. Another 50% of the power in the probe and pump laser beams is lost when the fiber optic pigtails 21 are joined together by optic coupler 28. Thus, the maximum power which could reach eye 40 is approximately 25 mW when starting with a laser power output of 100 mW.

Fiber optic coupler 28 combines the probe and modulated pump laser beams and directs them into an optional spatial filter 30. The spatial filter 30 converts the cross-section intensity to a Guassian Distribution which allows the beam to be focused more precisely and insures the complete combination of the two wavelengths before the laser beams are directed into the eye 40.

Figure 5:
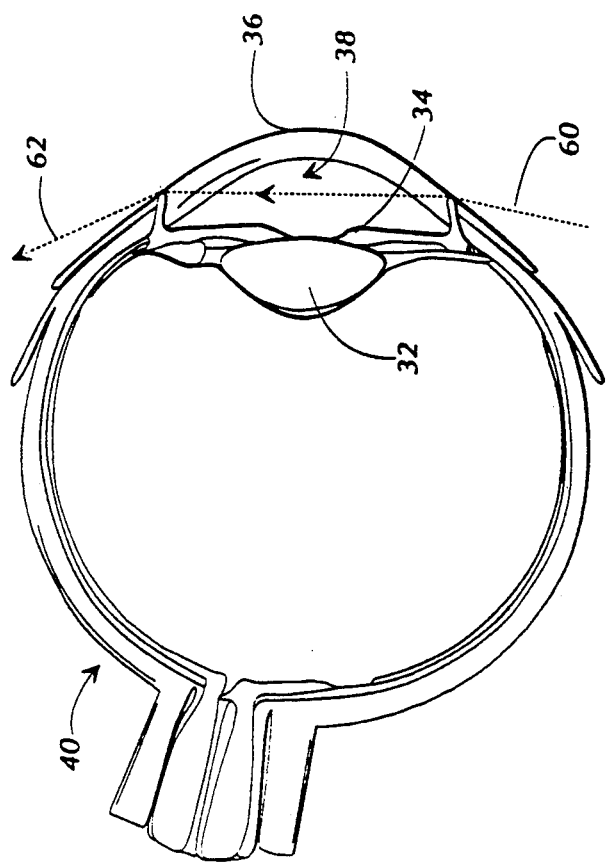
FIG. 5 is a top view of an eye showing entering and exiting laser beams.
Figure 6:
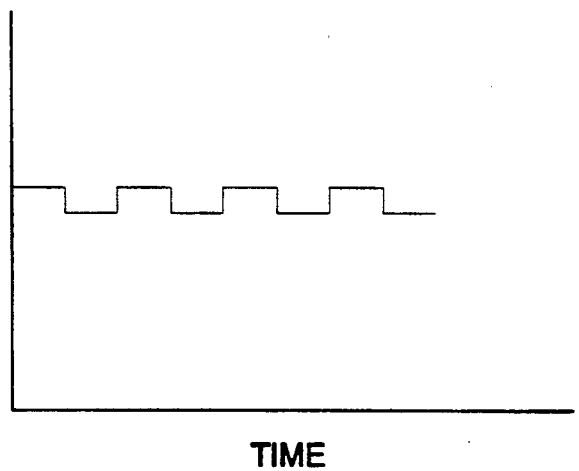
FIG. 6 illustrates the modulation of the detected probe laser power after extraction versus time.

The combined laser beams travel through fiber optic cables associated with means for delivering the laser beams to the eye, preferably in the form of a handset (not shown). The handset is held up against eye 40 and directs the probe and modulated pump laser beams into the ocular aqueous humor. The trajectory of incident laser beams 60 can be seen in FIG. 5. The laser beams 60 are passed through the cornea 36 and the aqueous humor 38 in such a manner as to bypass the lens 32 and the iris 34. Pump and probe beams 60 excite stimulated Raman radiation while inside the ocular aqueous humor 38. The scattered Raman radiation causes a small amount of the energy at the pump frequency to be shifted to the probe frequency, thereby inducing fluctuations in the previously constant power level of the probe laser beam, as illustrated in FIG. 6. These fluctuations in the probe laser beam power are directly related to the concentration of D-glucose in the ocular aqueous humor 38. The now modulated probe laser beam and the pump laser beam exit the eye and are coupled into an optical fiber in the handset-cable assembly.

The coupled detected laser beams are passed through a set of cascaded narrow band interference filters 42. These optional filters are centered at the probe wavelength plus or minus about 5 nm, thereby filtering the pump laser beam away from the probe laser beam. Thus, if the probe wavelength is set at 0.83 microns, the band width (BW) for the filters would be $BW = 825$ nm $< \lambda <$ 835 nm. The filters are cascaded because the desired reduction in the pump laser power cannot be achieved with a single filter. Further reduction in the power of the pump wavelength may be accomplished with a prism or grating. Thereafter, the modulated probe laser beam is applied to a photo-voltaic diode in photodetector/amplifier 44, which outputs an electrical signal. The photo-voltaic diode provides a current output in relation to the amount of light input. The photodetector/amplifier 44 includes a low-noise amplifier which amplifies the low current level output of the photo-voltaic diode to achieve a voltage level compatible with the circuitry of the synchronous detector 46. A transresistance gain of greater than $10^8$ is achieved by the low noise amplifier, which also filters off the large DC bias.

The operating band of the low noise amplifier is determined by the noise spectrum of the probe laser. The noise spectrum of the probe laser is relatively constant between 1–10 kHZ, and increases below this frequency range. Restricting the passband of the low noise amplifier to this frequency range helps eliminate undesired noise from the probe laser. Those skilled in the art will understand that the passband chosen depends upon the noise spectrum particular to the laser used as the probe laser. Different lasers may be expected to require different low noise amplifiers.

The output 45 of the photodetector/amplifier 44 is fed to synchronous detector 46, such as a Princeton HR-8 PAR lock-in amplifier. The synchronous detector 46 compares output 45 to the output 27 of signal generator 26, and generates signal 49, which is representative of the concentration of D-glucose in the ocular aqueous humor. The synchronous detector output 49 may then be fed to any standard display element.

Use of the lock-in amplifier involves using the pump laser modulation signal as an external reference signal and feeding the SRS signal into the signal input of the amplifier. The bandpass filter for the external reference may need to be tuned to the pump modulation frequency depending on the model of the lock-in amp. A phase offset between the reference and the SRS signal should be zeroed as indicated in the installation manual. Then the appropriate gain setting for the SRS input signal should be set. The time constant or integration time setting may vary depending upon the noise present on the signal. The DC output signal may be read from the meter in the unit or directed to an external display.

An alternative, and more costly method of generating a representative electrical signal from the photodetector/amplifier 44 output is to feed output 45 to a dynamic signal analyzer 48, such as an HP 3561 made by Hewlett-Packard. Analyzer 48 measures the power contained in the detected probe laser beam at the modulation frequency. This power is likewise related to the D-glucose concentration. Thus, it is possible to use at least two independent methods to calculate the D-glucose concentration.

The procedure for the dynamic signal analyzer involves connecting the SRS signal to the input jack of the analyzer. The soft key programming is generally discussed in the user's manual for the analyzer. The frequency span should be set to a center frequency equal the pump modulation frequency and a span of about 100 Hz which may vary depending upon signal noise. Preferably, the unit should also be programmed to RMS average 50 samples. There is a setting for peak tracking which will display a numerical value for the frequency peak in the local portion of the signal spectrum which is currently displayed. The vertical scale units should be set to "linear" and thus the value for the SRS signal corresponding to the glucose concentration will be the value of the peak frequency component. The numerical value is displayed on the screen of the analyzer.

Before using the apparatus of the present invention background measurements should be made to establish a signal reference point and to be certain that there are no spurious signals in the passband of the low noise amplifier which forms part of the photodetector/amplifier 44. A noise spectrum measured by the synchronous detector 46 with only the probe laser turned on should be made. Another important background measurement is pump laser power "leakthrough". Although the two narrow band interference filters filter the pump wavelength, some small amount of pump power still reaches the detector 46. Since this signal is present whenever the pump laser is on, it will offset other measurements. In addition to the presence of pump leakthrough, stimulated Raman scattering takes place in the fiber optic cables 21 which carry the input power to the eye 40 and this SRS signal offsets the SRS signal from D-glucose in the ocular aqueous humor. These offset signals do not directly limit the sensitivity of the D-glucose measurement since the SRS signal from the D-glucose adds to the offset signals and thus the offset signals can be subtracted out in the calculation of the D-glucose concentration. But the relative amplitude of these offset signals does limit the detector gain which ultimately limits the system sensitivity.

Occurring naturally in the ocular aqueous humor, water is also a Raman-active molecule. There is no peak present in the Raman spectrum for water at the frequency shift of 518 $cm^{-1}$; even so, some broad features of the water spectrum will produce an SRS signal at a shift of 518 $cm^{-1}$. This SRS signal from water contributes to the offset signal and should be subtracted out in the calculation of D-glucose concentration.

Figure 7:
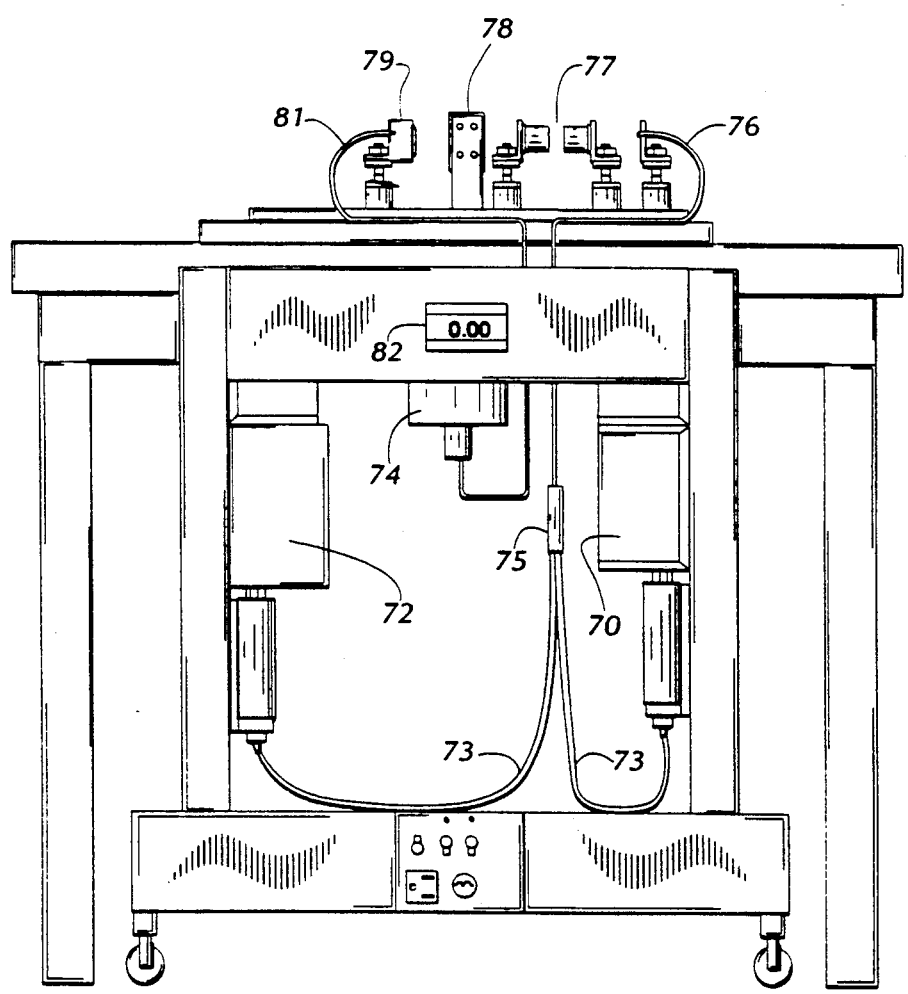
FIG. 7 illustrates the apparatus of the present invention for in vivo measurement.

A schematic of the present invention for in vitro measurement can be seen in FIG. 7. The entire apparatus is mounted on a wheeled cart 68. The pump laser (SDL-2412-H2) and its power supply 72 are mounted vertically on one side of the cart, while the probe laser (SDL-2412-H2) and its power supply 70 are mounted vertically on the opposite side of the cart. The preferred power supply for the probe laser is an LDX 3620 by ILX lightwave, Montana, because of its low noise current to the laser diode and constant power mode having an automatic compensation feature. Outputs from each of the pump and probe lasers are fed by optical fiber pigtails 73 to a fiber optic coupler 75. The pigtails are multi-mode fiber optic cables to match those supplied with the lasers. The combined probe and pump laser beams are then fed by fiber optic cables 76 from the fiber optic coupler 75 up to the spatial filter 77 and from there into an eye, or alternatively, into a glucose test cell 78, shown in place on a table behind the cart. The spatial filter 77 is preferably a Model 900 from Newport Optics. Glucose test cells 78 are used for in vitro measurement. The test cell 78 is machined plastic with special windows of a high quality, low impurity glass with a special coating to reduce reflections of optical wavelengths selected for the lasers. Preferred coatings include a magnesium fluoride or a coating broadband near infrared coating like Newport #Ar.16.

A set of interference filters 79, previously described, receive the pump and probe laser beams as they exit the glucose cell 78. Fiber optic cable 81 passes the detected laser beams from filters 79 to detector unit 74, which houses both the photo-voltaic diode and the low noise amplifier. The output from the detector unit 74 is then fed to the synchronous detection unit. A switchable laser temperature readout 82 may be provided to monitor the output of lasers 70, 72.

Figure 8:
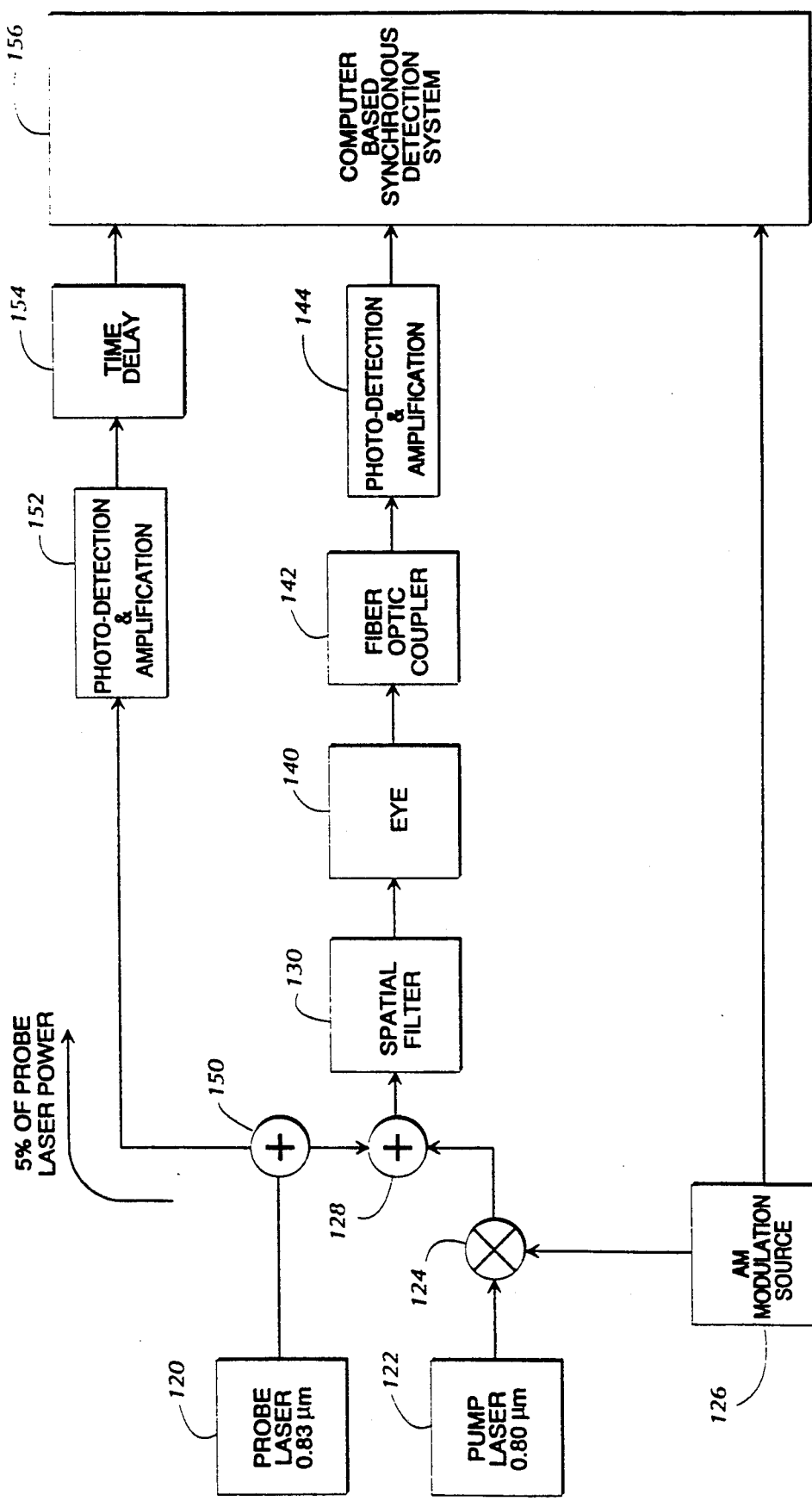
FIG. 8 is a block diagram an alternative embodiment of the present invention.

A block diagram of an alternative embodiment of the present invention is shown in FIG. 8. The alternative apparatus incorporates both a probe laser 120 and a pump laser 122. These lasers are both monochromatic and both operate at the same wavelengths discussed hereinabove with respect to the preferred embodiment of FIG. 3. The pump laser 122 is modulated using an AM modulation source 126, such as Hp 3314A.

The output of probe laser 120 is connected to an optical coupler 150 which is reversed to split the probe laser output into two beams, one containing 5% and the other containing 95% of the probe laser power.

Another fiber optic coupler 128 combines ninety-five percent of the probe laser power with the modulated pump laser beam and outputs the combined beams to spatial filter 130. Using a handset (not shown) the combined beams are then directed into the eye 140. Inside the ocular aqueous humor of the eye 140 stimulated Raman radiation causes a portion of the power at the pump frequency to be shifted to the probe frequency, thereby modulating the probe laser beam. As the pump probe beams exit the eye they are coupled into a fiber optic cable to transport the SRS optical signal to the photo detector. The pump laser beam is filtered from the probe laser beam using a series of narrow band filters incorporated into the photodetector/amplifier 144. The modulated pump probe laser beam is then transduced from an optical signal into an electrical signal using a photo-voltaic diode. The electrical output from this diode is thereafter amplified using an extremely large gain, low noise amplifier incorporated in photodetector/amplifier 144 to achieve the signal levels compatible with a detection scheme. The amplifier's gain is on the order of $10^8$. The amplifier's passband corresponds to a frequency range in which the probe laser's noise spectrum is substantially constant. The output of the photodetector/amplifier 144 is then fed into a computer-based synchronous detector 156.

Five percent of the probe laser power is applied to the photodetector/amplifier 152, which is substantially similar to photodetector and amplifier 144 and which generates an electrical signal representative of the probe laser beam power. This output may then be fed to an optional time delay 154 to compensate for the delay of the laser beam through the spatial filter, fiber optic coupler and photodetector amplifier path. However, since this time delay is small and is physically hard to realize, time delay 154 may also be eliminated without substantially effecting the accuracy of the D-glucose measurement.

The computer-based synchronous detector 156 compares the photodetector/amplifier output 144 with the output of the AM modulator 126 and photodetector/amplifier 152 output, allowing the computer-based synchronous detector 156 to compensate for amplitude variations in the probe laser beam caused by internal noise and thermal drift of the probe laser. A data acquisition/interface board to the computer connects the signals from photodetector/amplifiers 144, 152 to the computer. The data acquisition/interface board preferably consists of 3 primary A/D channels. Two of these channels are 16-bit resolution and the third channel is only 8-bit resolution. The 16-bit channels are used to convert the SRS signal and the PROBE Noise signal, while the 8-bit channel converts the modulation signal. The specifications should meet or exceed the following:

16-bit Converters—Analog Devices (1376A)
16-bit Track-Hold—Analog Devices (389KD)
Amplifiers
8-bit Converter—Analog Devices (574A)
8-bit Track-Hold—Analog Devices (HTC-0300)

A sampling rate of 10 KHz is used so the Nyquist frequency is 5 KHz. Appropriate anti-aliasing filters should be used prior to conversion which limit the bandwidth of the input signals to ≦5KHz. Also there are four secondary A/D inputs to monitor various background activities like laser temperature. Once the analog signals are converted to digital values they are converted to floating point numbers and stored in memory arrays by low level programming. Currently the data is processed by algorithms to yield a stable SRS value for a given glucose concentration. These algorithms include the following:

1) The use of infinite impulse response (IIR) filters, such as a Butterworth filter, to further narrow the bandwidth of the signal.
2) The subtraction of amplitude noise originating on the PROBE Laser.
3) A conventional cross-correlation algorithm to yield a final result.

An alternate approach to the optical fiber band system described above would be to use entirely bulk optics in the system, thus eliminating the optical fibers completely. This bulk optics implementation, although more costly, will yield a higher system sensitivity than the optical fiber based system. This arises from the elimination of one of the sources of "leak through" signals and the conversion to single-mode laser diodes. Current technology limits the use of these high power single-mode laser diodes to a bulk optic system. These single-mode laser diodes concentrate their optical power into a much narrower spectral line which will greatly improve the SRS signal to noise ratio.

Figure 9:
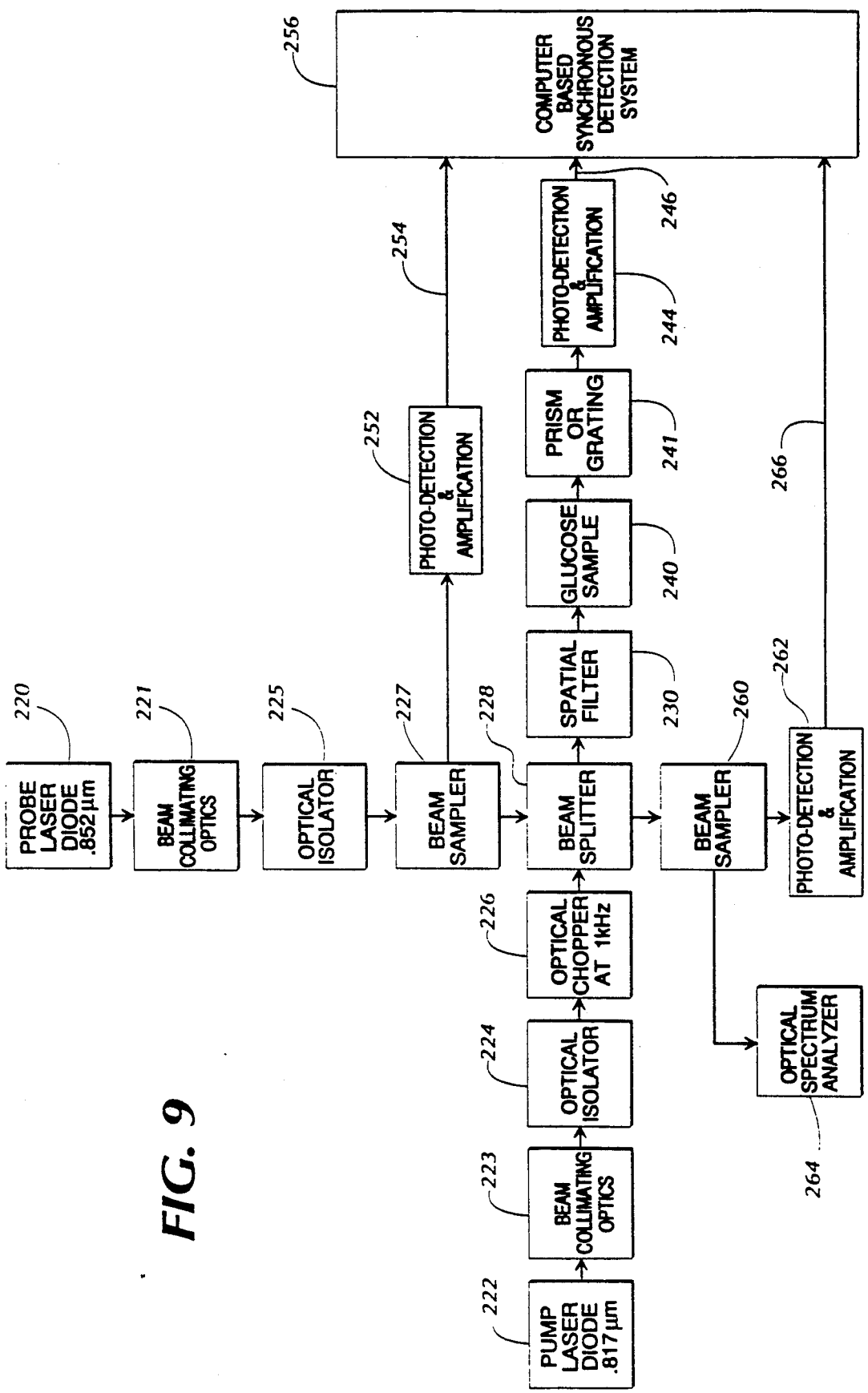
FIG. 9 is a block diagram of another alternate embodiment of the present invention using bulk optics.

As illustrated in FIG. 9, the output of each laser 220,222 of the bulk optic system is delivered to beam collimating optics 221, 223, which preferably consist of a pair of cylindric lenses for each laser, to focus the laser beam along their orthogonal axes to make a collimated beam from the asymmetrical cone shaped output of the lasers. Optical isolators 224, 225 are provided to prevent reflection of the beams back into the lasers. The isolators can be broad band isolators covering the band width of 750 to 950 nm, such as the Newport ISO-7885 optical isolator. The output of pump laser 222 passing through optical isolator 224 is delivered to an optical chopper 226 or electric optic modulator which preferably operates at 1 kHz, though may be operated at different frequencies depending on the modulation desired for the pump laser output. Beam samplers 227, 260 are provided to reflect a small sample portion of the beam or beams, the amount of the sample depending upon the angle of placement of the beam sampler in the path of the beam. Beam sampler 227 is used to provide a small sample of the probe laser output to the photodetector and amplifier 252, the output of which 254 provides a probe laser noise signal to the computer based synchronous detection system 256. Beam sampler 260 provides a small sample of the beams provided to the spatial filter 230. The output of the photodetector and amplifier 262 coupled with the beam sampler 260 provides a synchronous detection reference signal 266 to the computer based synchronous system 256. An optical spectrum analyzer 264 is used to monitor the beams provided to the spatial filter 230 in the laboratory setting because the single mode lasers have a tendency to "mode hop" and change the wavelength of their output.

The rest of the path in FIG. 9 beginning with the spatial filter 230, the glucose sample 40 through to the computer based synchronous detection system 256 is the same as the embodiments discussed above with the exception of the addition of the prism or grading 241. If a prism is used, a standard dispersing prism is preferred.

From the bulk optic system block diagram of FIG. 9 one can see that this system is functionally equivalent to the optical fiber based system. The major differences between the two implementations are as follows:

1) Now of the polarization of the optical fields must be carefully controlled. It is vitally important that both the pump laser wavelength and the probe laser wavelength have nearly the same polarization of their optical fields. Here linear polarization is maintained throughout the system.

2) Due to technological limitations, the pump single-mode laser diode's optical power cannot be modulated by the modulation of its current. This is due to the fact that the wavelength of the laser diode's output power does depend upon its current. Thus, both laser diodes are operated with a constant current source. Now the pump laser's optical power is modulated by an optical chopper 226 which yields an equivalent optical power modulation to the optical fiber based system.

3) A key addition to this system is an optical isolator 224, 225 which is used with each laser diode to minimize reflections of the optical power back into the laser cavity. This is very important since the reflected power can cause the laser diode to change its wavelength during operation. This phenomenon has been observed in the optical fiber based system.

4) The spatial filter 230 is now required to insure that the optical power from each laser is collinearly focused through the glucose solution 240. The glucose solution may be in an optical test cell or in the ocular aqueous humor.

The addition of the optical spectrum analyzer 264 is optional. Its purpose is to monitor a portion of the optical power to insure the proper optical wavelengths are present. Also the wavelengths for the single-mode laser diode have been changed slightly due to the availability from the manufacturer. The difference between these two wavelengths still corresponds to a frequency difference of 518 cm$^{-1}$ as previously discussed.

It will be obvious to those skilled in the art that many variations may be made in the embodiment chosen for the purpose of illustrating the best mode of making and operating the present invention, without departing from the scope thereof as defined by the appended claims.

We claim:

1. A method of non-invasively measuring the concentration of a Raman active molecule in ocular aqueous humor using stimulated Raman spectroscopy, comprising the steps of:
   generating a modulation signal;
   emitting a probe laser beam having a first wavelength;
   emitting a pump laser beam having a second wavelength differing from said first wavelength by a third wavelength selected to be within a characteristic Raman shift spectrum for the Raman active molecule;
   modulating said pump laser beam using said modulation signal;
   directing said probe laser beam and said modulated pump laser beam into the ocular aqueous humor thereby stimulating Raman scattered radiation, said Raman scattered radiation inducing fluctuations in said probe laser beam, said fluctuations being related to the concentration of the Raman active molecule in the ocular aqueous humor, said probe laser beam exiting the ocular aqueous humor;
   detecting said probe laser beam after it exits the ocular aqueous humor;
   converting said detected probe laser beam into a Raman electrical signal; and
   producing a signal representative of the concentration of the Raman active molecule in the ocular aqueous humor from said Raman electrical signal and said modulation signal.

2. The method of claim 1 wherein said Raman active molecule is D-glucose.

3. The method of claim 2 wherein said first wavelength is about 0.83 μm.

4. The method of claim 3 wherein said second wavelength is about 0.8 μm.

5. The method of claim 1 wherein the step of modulating said pump laser beam comprises amplitude modulating said pump laser beam.

6. The method of claim 5 wherein said step of emitting the probe laser beam includes maintaining the power output of the probe laser beam substantially constant.

7. The method of claim 1 further comprising the step of spatially filtering said probe laser beam and said modulated pump laser beam before said directing step.

8. The method of claim 1 further comprising the step of amplifying said Raman electrical signal.

9. The method of claim 1 wherein the step of producing a signal representative of the Raman active molecule includes digital signal analyzing the Raman electrical signal to produce an electrical signal representative of the concentration of the Raman active molecule.

10. The method of claim 1 wherein the step of producing a signal representative of the Raman active molecule includes use of a synchronous detector to produce the signal representative of the Raman active molecule.

11. The method of claim 1 wherein the power output of the pump laser is maintained at a higher level than the power output of the probe laser beam.

12. An apparatus for non-invasively measuring the concentration of an Raman active molecule in ocular aqueous humor using stimulated Raman spectroscopy, comprising:
means for generating a modulation signal;
means for emitting a probe laser beam having a first wavelength;
means for emitting a pump laser beam having a second wavelength differing from said first wavelength by a third wavelength selected to be within a characteristic Raman shift spectrum for the Raman active molecule;
modulating means for modulating said pump laser beam using said modulation signal;
means for directing said probe laser beam and said modulated pump laser beam into the ocular aqueous humor thereby stimulating Raman scattered radiation, said Raman scattered radiation inducing fluctuations in said probe laser beam said fluctuation being related to the concentration of the Raman active molecule in the ocular aqueous humor; said probe laser beam exiting the ocular aqueous humor;
means for detecting the probe laser beam after it exits the ocular aqueous humor;
means for converting said detected probe laser beam into a Raman electrical signal; and
means for producing a signal representative of the concentration of the Raman active molecule in the ocular aqueous humor from said modulation signal and said Raman electrical signal.

13. The apparatus of claim 12 wherein said first wavelength is about 0.83 $\mu$m.

14. The apparatus of claim 13 wherein said second is about 0.8 $\mu$m.

15. The apparatus of claim 12 wherein said means for emitting said probe laser beam comprises a first monochromatic laser.

16. The apparatus of claim 12 wherein said means for emitting said pump laser beam comprises a second monochromatic laser.

17. The apparatus of claim 12 wherein said means for directing includes a fiber optic coupler and fiber optic cable.

18. The apparatus of claim 12 further comprising means for amplifying said Raman electrical signal.

19. The apparatus of claim 12 further comprising means for digital signal analysis of said detected probe laser beam to produce an electrical signal representative of the Raman active molecule.

20. The apparatus of claim 12 wherein said means for detecting and said means for converting comprise a photodetector.

21. The apparatus of claim 12 wherein said means for producing said signal representative of the Raman active molecule comprises a synchronous detector.

22. The apparatus of claim 21 wherein said modulating means comprises an amplitude modulator.

23. The apparatus of claim 21 wherein said means for detecting comprises a dynamic signal analyzer.

24. The apparatus of claim 12 wherein said means for said signal representative of said Raman active molecule comprises a dynamic signal analyzer.

25. The apparatus of claim 24 wherein said wavelength is about 0.83 $\mu$m.

26. The apparatus of claim 12 wherein said means for producing said signal representative of said Raman active molecule comprises a computer based synchronous detection system.

27. The apparatus of claim 26 wherein said second wavelength is about 0.8 $\mu$m.

28. The apparatus of claim 12 wherein the means for emitting a probe laser beam includes a power supply for maintaining the output of the probe laser substantially constant.

29. The apparatus of claim 12 wherein the signal representative of said Raman active molecule is representative of the concentration of said Raman active molecule.

30. The apparatus of claim 29 wherein said means for emitting a probe laser beam emits said probe laser beam having a substantially constant amplitude.

31. An apparatus for non-invasively measuring the concentration of a Raman active molecule in the ocular aqueous humour, comprising:
a probe laser emitting a probe laser beam, having a first wavelength;
a pump laser emitting a pump laser beam, having a second wavelength which second wavelength differs from said first wavelength by an amount selected to be within a characteristic Raman shift spectrum for the Raman active molecule;
a modulator means for producing a modulation signal and for modulating said pump laser beam;
a fiber optic coupler receiving said probe laser beam and said modulated pump laser beam and directing said laser beams into the ocular aqueous humor thereby stimulating Raman scattered radiation, said Raman radiation inducing fluctuations in said probe laser beam, said fluctuations being related to the concentration of the Raman active molecule in the ocular aqueous humor, said probe laser beam exiting the ocular aqueous humor;
a photodetector receiving said probe laser beam and producing an electrical signal; and
an amplifier means for developing a dc voltage representative of the concentration of the Raman active molecule in the ocular aqueous humor from said electrical signal and
said modulation signal.

32. The apparatus of claim 31 wherein said photodetector comprise a synchronous detector.

* * * * *